United States Patent
Rydin et al.

[11] Patent Number: 6,095,496
[45] Date of Patent: Aug. 1, 2000

[54] VALVE FOR REGULATING A GAS FLOW

[75] Inventors: Göran Rydin; Per-Göran Eriksson, both of Täby; Göran Rydgren, Bunkeflostrand, all of Sweden

[73] Assignee: Siemens Elema AB, Solna, Sweden

[21] Appl. No.: 09/209,684

[22] Filed: Dec. 11, 1998

[30] Foreign Application Priority Data

Dec. 15, 1997 [SE] Sweden ................................. 9704660

[51] Int. Cl.⁷ ........................................................ F16K 7/12
[52] U.S. Cl. ............................ 251/331; 251/205; 251/120
[58] Field of Search ..................................... 251/331, 359, 251/333, 205, 129.17, 120

[56] References Cited

U.S. PATENT DOCUMENTS

| | | |
|---|---|---|
| 4,741,510 | 5/1988 | Baumann ................................. 251/205 |
| 5,127,625 | 7/1992 | Kleinhappl . |
| 5,265,594 | 11/1993 | Olsson et al. . |
| 5,265,843 | 11/1993 | Kleinhappl . |

FOREIGN PATENT DOCUMENTS 33 42 482   6/1983   Germany .

*Primary Examiner*—Kevin Lee
*Attorney, Agent, or Firm*—Hill & Simpson

[57] ABSTRACT

A valve for regulating a gas flow has a valve housing with an inlet for the gas to be regulated, an outlet for a regulated gas flow, a valve seat with a valve opening, and a movable sealing part with a controllable shaft, the terminal side of the sealing part making and breaking a seal between the valve seat and the sealing part such that the sealing part closes and opens the valve opening and regulates the gas flow through the valve opening. In order to allow particularly small gas flows to be repeatedly regulated with high precision and a large dynamic, the plane of the terminal side of the sealing part and the plane of the valve seat form a non-zero angle, allowing the terminal side of the sealing part to press against the valve seat, or to detach therefrom, so that the terminal side gradually closes and opens the valve opening. Alternatively a preformed part is attached between the terminal side of the sealing part and the valve seat, this part being arranged obliquely relative to the valve seat and having a surface area which corresponds to at least the surface area of the valve seat. The terminal side of the sealing part is arranged such that it presses the obliquely arranged part against the valve seat, or detaches it therefrom such that the obliquely arranged part gradually closes or opens the valve opening.

8 Claims, 5 Drawing Sheets

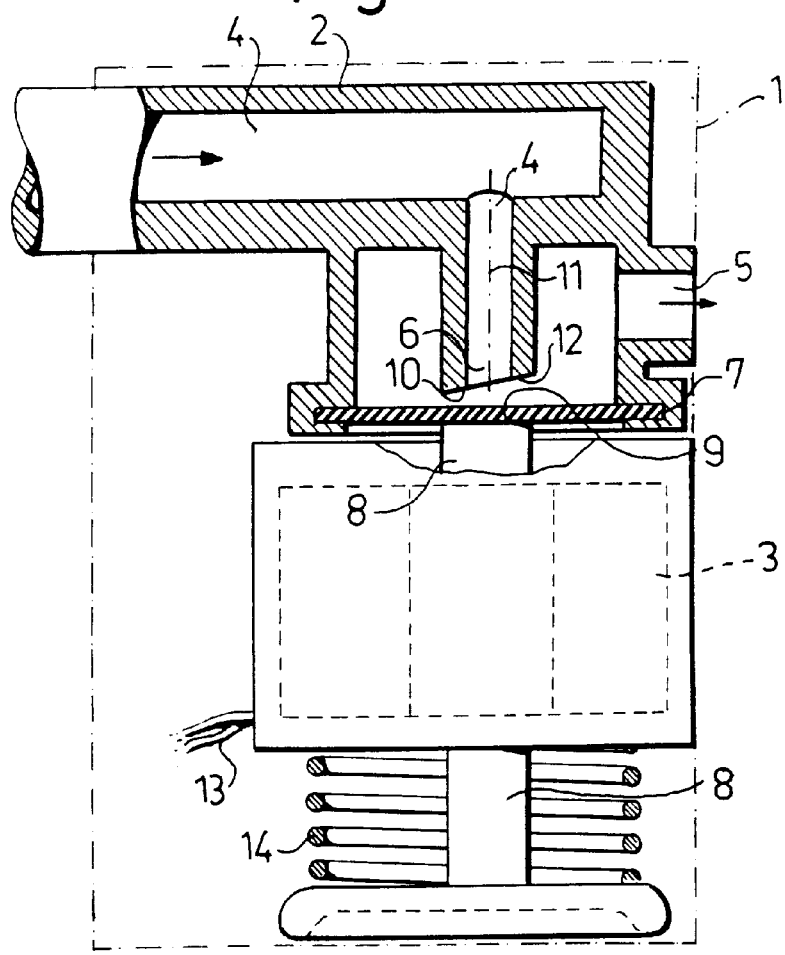
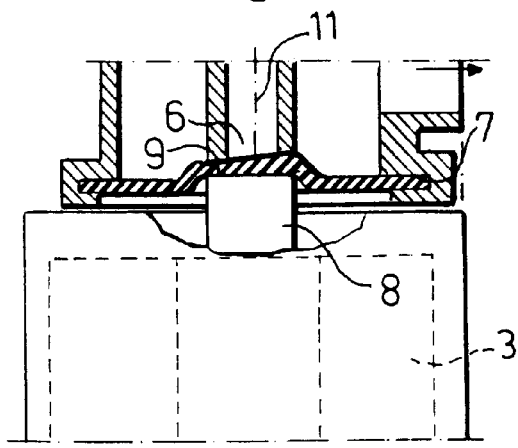
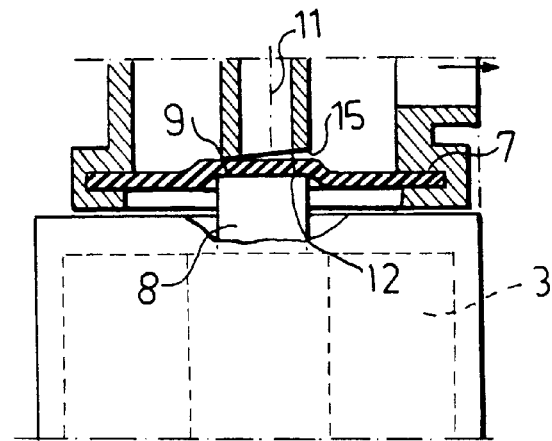

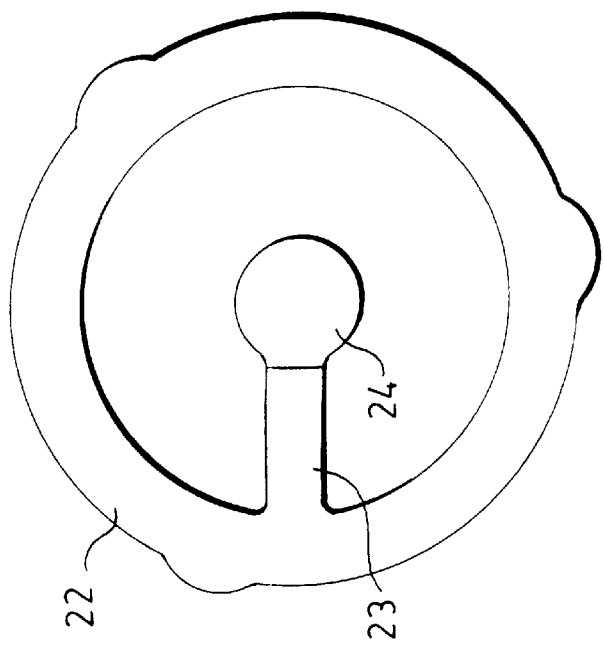
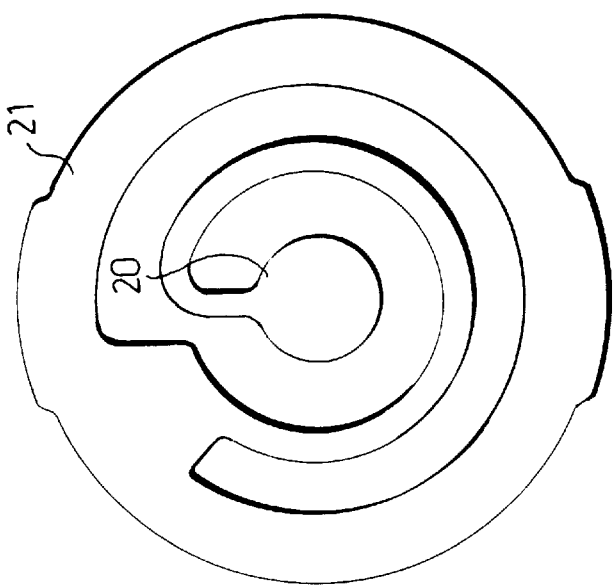
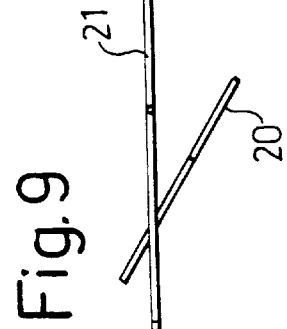

VALVE FOR REGULATING A GAS FLOW

BACKGROUND OF THE INVENTION

1. Field of the Invention

The present invention relates to a valve for regulating a gas flow of the type having a valve housing with an inlet for the gas to be regulated and an outlet for a regulated gas flow, a valve seat with a valve opening, and a movable sealing actuator having a controllable shaft, wherein the terminal side of the sealing part can influence a seal element arranged between the valve seat and the sealing part such that the sealing actuator closes and opens the valve opening and regulates the gas flow through the valve opening.

2. Description of the Prior Art

A valve of this type is depicted and described in U.S. Pat. No. 5,265,594. In connection with the supplying of gas to a patient connected to a breathing device it is very important that large as well as small amounts of gas be regulated with high precision and reproducibility by means of such a valve. Ideally to achieve this it is necessary that the seal element, which is a membrane drawn tight at the valve housing in the value of this reference, be lifted parallel to the valve seat in the opening thereof, and be pressed against the valve seat by the shaft end of the actuator with a uniformly distributed force in the closing of said valve seat. Even if such a shaft—a solenoid shaft in this reference—causes the membrane to follow an apparently perfect pattern of motion such as this, problems can arise, particularly in connection with the opening of the valve opening, when the membrane is supposed to come loose from the valve seat. For example, problems can arise as a result of wear or aging of the membrane, and if the membrane gets hung up in a first instant of movement and then abruptly opens, whereby a precise and repeated control of the flow can be difficult to achieve, particularly in connection with small amounts. The delay or the hysteresis which can arise in the magnetization of the solenoid shaft in the activation thereof can also cause an undesirable control of the gas flow in connection with the opening of the valve opening, with the abovementioned adverse effects.

SUMMARY OF THE INVENTION

It is an object of the present invention is to provide a valve of the abovementioned type in which particularly small gas flows can be repeatedly regulated with greater precision and greater dynamics.

This object is inventively achieved in a valve wherein the plane of the terminal side of the sealing actuator and the plane of the valve seat form an angle, it being possible to press the terminal side of the sealing part against the valve seat, or to loosen it therefrom, such that the terminal side gradually closes or opens the valve opening. Due to the non-zero angle a gap is always formed between the seal element and the valve seat or, if the seal element is attached at the valve seat, between the seal element and the terminal side of the sealing actuator, at the moment of opening or closing. This gap extends over a relatively small part of the contact surface of the seal element, or the valve seat, so that a gradual opening or closing of the valve opening ensues without the valve being abruptly opened or closed. It is thereby guaranteed that not only large but also small gas flows can be repeatedly regulated with high precision and with a large dynamic.

In an embodiment of the inventive valve, the plane of the valve seat is situated obliquely in relation to the center axis of the valve seat. In such an embodiment the plane of the terminal side of the sealing actuator is situated perpendicularly to the center axis of the actuator.

In another embodiment of the inventive valve, the plane of the terminal side of the sealing actuator is situated obliquely in relation to the center axis of the part.

The angle between said planes can inventively be between 0.3° and 2°, preferably 0.7°. This angle is preferably matched to the size of the valve opening and the strength of the seal.

In a further embodiment of the inventive valve, the seal is a membrane drawn tight at the valve housing and the membrane is provided with a rigid planar plate which is arranged exactly in front of the valve seat and which has a surface area at least as large as the surface area of the valve seat. Also, the part of the terminal side of the sealing actuator which influences the membrane has a surface area which is smaller than the surface area of the valve seat. Dependent on the surface area of that part of the terminal side of the sealing actuator which influences the membrane, or the plate, the rigid plate can tilt against said terminal side in the closing and opening of the valve opening, allowing the valve opening to be gradually closed or opened by the plate. The plate is preferably integrated in the membrane, but can alternatively be glued to the membrane. This structure of the membrane allows the plane of the valve seat to have a relatively large angle to the center axis, if desired. Furthermore, even if the membrane is partially deformed, there is always a gradual opening and closing of the valve seat due to the fact that the plate can tilt against the terminal side of the sealing actuator. The terminal side of the sealing actuator is preferably rounded.

The above object is also achieved in accordance with the invention in a valve having a preformed part which is arranged obliquely relative to the valve seat, which is attached between the terminal side of the sealing actuator and the valve seat, this preformed part corresponding at least to the surface area of the valve seat. The terminal side of the sealing part is arranged such that it presses the obliquely arranged preformed part against the valve seat, or respectively, loosens it from the valve seat such that the obliquely arranged preformed part gradually closes or opens the valve opening. The advantages mentioned in connection with the aforementioned planes which form a non-zero angle are obtained with such an obliquely arranged preformed part. Due to the obliquely arranged preformed part the plane of the terminal side of the sealing actuator or the plane of the valve seat do not need to be angled in relation to their center axes.

In a further version of this embodiment the part of the terminal side of the sealing actuator which influences the obliquely arranged part has a surface area that is smaller than the surface area of the valve seat. The terminal side is preferably constructed in rounded fashion. Thus there is always a gradual opening and closing of the valve seat, even if the seal element may possibly become deformed.

In an another version of this embodiment of the inventive valve, the obliquely arranged part is a part of a spiral disk, the disk being secured at the valve housing. This allows the disk, and thus the obliquely arranged part as well, to be separate parts which can be replaced as needed.

The obliquely arranged part can be a part of a leaf spring, with the leaf spring being secured at the valve housing. The obliquely arranged part thus also can be replaced as needed.

The obliquely arranged part inventively has an angle of between 5° and 40°, preferably 30° relative to the plane of the disk, or relative to the leaf spring.

DESCRIPTION OF THE DRAWINGS

FIG. 1 is a side view partly in section, of an inventive valve, with a sealing actuator in a position in which the valve opening is open.

FIGS. 2 and 3 respectively show a partial section through a valve according to FIG. 1, with the sealing actuator in different positions.

FIG. 8 is a plan view of a disk, with a part which is provided in connection with the sealing actuator depicted in FIG. 6 and FIG. 7.

FIG. 9 is a side view of a disk according to FIG. 8.

FIG. 10 is a plan view of another disk, with a part which is provided in connection with the sealing actuator depicted in FIG. 6 and FIG. 7.

FIG. 11 is a side view of the disk of FIG. 10.

DESCRIPTION OF THE PREFERRED EMBODIMENTS

Figure 4:
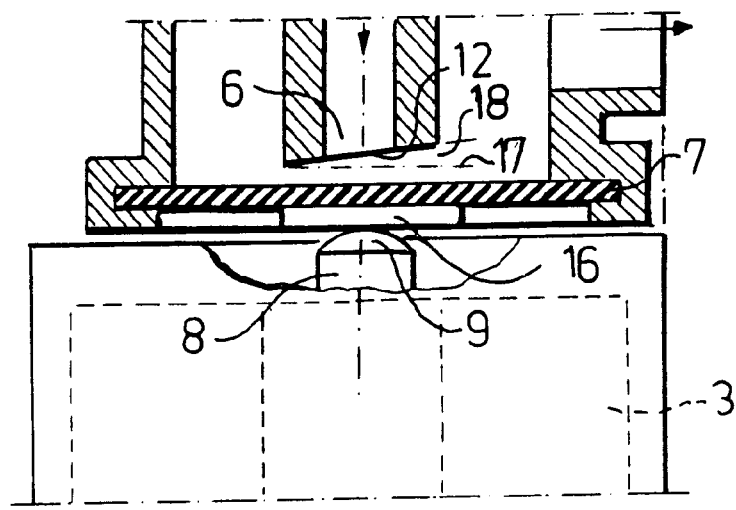
FIG. 4 is a partial section through a valve according to FIG. 1, with a different embodiment of the sealing element than that in FIG. 1 to FIG. 3.

FIG. 1 depicts, partly in section, one embodiment of an inventive valve. The valve is depicted in FIG. 1 in an open position. The valve has a valve shell 1 in which a valve housing 2 and a solenoid 3 are arranged. The valve housing 2 is provided with a through-channel for a gas flow which is to be regulated, the channel being divided into an inlet 4, an outlet 5 and an intermediately arranged valve opening 6 with a valve seat 12. A sealing element in the format of a membrane 7 is attached directly opposite the valve opening 6, the membrane 7 being drawn tight at the valve housing 2 and serving to regulate, by interaction with the terminal side 9 of a solenoid shaft 8 serving as a sealing actuator, the gas flow to a patient connected to a ventilator (not depicted). FIG. 1 shows that the plane 10 for the valve seat 12 has an oblique orientation relative to its center axis 11, so that the plane of the terminal side 9 of the solenoid shaft 8 and the plane 10 of the valve seat 12 thus form an angle. The angle between these planes is between 0.3° and 2°, preferably 0.7°.

To achieve an open valve position as depicted in FIG. 1 more or less current is fed to the solenoid 3 via a cable 13. The shaft 8 is thereby drawn into the solenoid housing, i.e. downward in FIG. 1, causing the membrane 7 to lift in the desired fashion from the valve seat 12 by the spring (elastic) force of the material and by the gas pressure on the inlet side, so that the gas can flow to the patient via the valve opening 6 and via the outlet 5. When the current supply to the solenoid 3 is switched off, its shaft 8 is no longer electromagnetically biased, but the shaft 8 is pressed against the membrane 7 with a sufficient force against the valve seat 12 by a pressure spring 14, so that the valve opening 6 is closed, as depicted in FIG. 2. A desirable safety aspect is thereby achieved; namely, given a power failure the valve closes and an uncontrolled release of gas to the patient is prevented.

FIG. 3 shows that in the opening of the valve opening 6, the membrane 7 first lifts from that portion of the valve seat 12 which has the largest distance to the terminal side 9 of the solenoid shaft 8. A gap 15 between the valve seat 12 and the membrane 7 thus always is formed at this part at the moment of opening. The membrane 7 can now gradually open the valve opening 6 by means of the described orientation of the valve seat 12. In the closing of the valve opening 6, the membrane 7 is gradually pressed against the valve seat 12 by the shaft end 9, so the gap 15 again arises before the membrane 7 finally seals against the valve seat 12.

In another exemplary embodiment, depicted in FIG. 4, the side of the membrane 7 opposite from the side facing the valve seat 12 is provided with a rigid, planar plate 16. The plate 16 has a surface area which is somewhat larger than the surface area of the valve seat 12. FIG. 1 shows that the end 9 of the solenoid shaft 8 abuts against the plate 16, the shaft end 9 preferably being constructed in rounded fashion. The valve opening 6 is shown in an open position. In the closing of the valve opening 6, if the membrane 7 is pushed via the shaft end 9 in the direction of the obliquely preformed valve seat 12, then the membrane 7 first rests against the portion of the valve seat 12 having the shortest distance to the membrane 7. The plate 16, and with it the membrane 7, subsequently tilts against the rounded shaft end 9, so that the membrane 7 is gradually pressed tight against the valve seat 12. The dashed lines 17 between the valve seat 12 and the membrane 7 illustrate this. In the opening of the valve opening 6 the plate 16, and with it the membrane 7, tilts against the rounded shaft end 9, so the membrane 7 can gradually break its contact with the valve seat 12. A gap 18 between the valve seat 12 and the membrane 7 arises not only at the moment of closing, but also at the moment of opening. The plate 16 alternatively can also be integrated in the membrane 7, as the dashed lines indicate.

Figure 5:
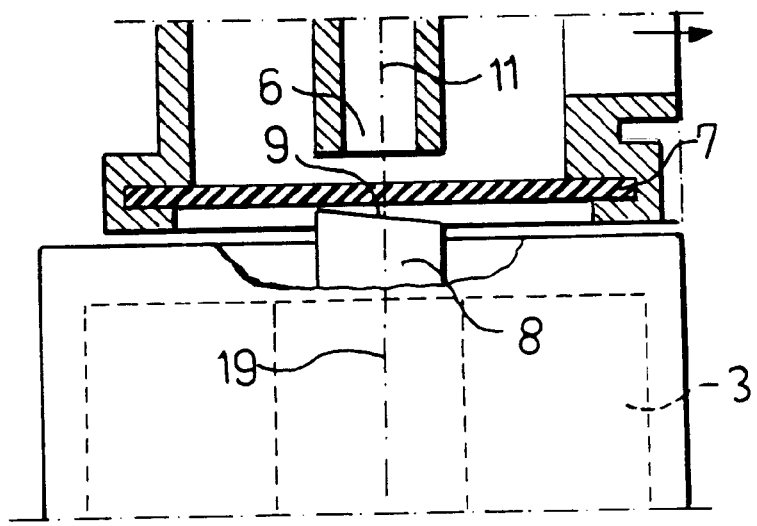
FIG. 5 is a partial section through a valve according to FIG. 1, with another embodiment of the sealing actuator.

FIG. 5 depicts another exemplary embodiment in which the plane of the terminal side 9 of the solenoid shaft 8 has a formation which is oblique in relation to the center axis 19. In such a case the plane of the valve seat 12 is situated perpendicularly to its center axis 11. The procedure in the opening and closing of the valve opening 6 is approximately the same as has been described, particularly in connection with the FIGS. 1 to 3.

Figure 6:
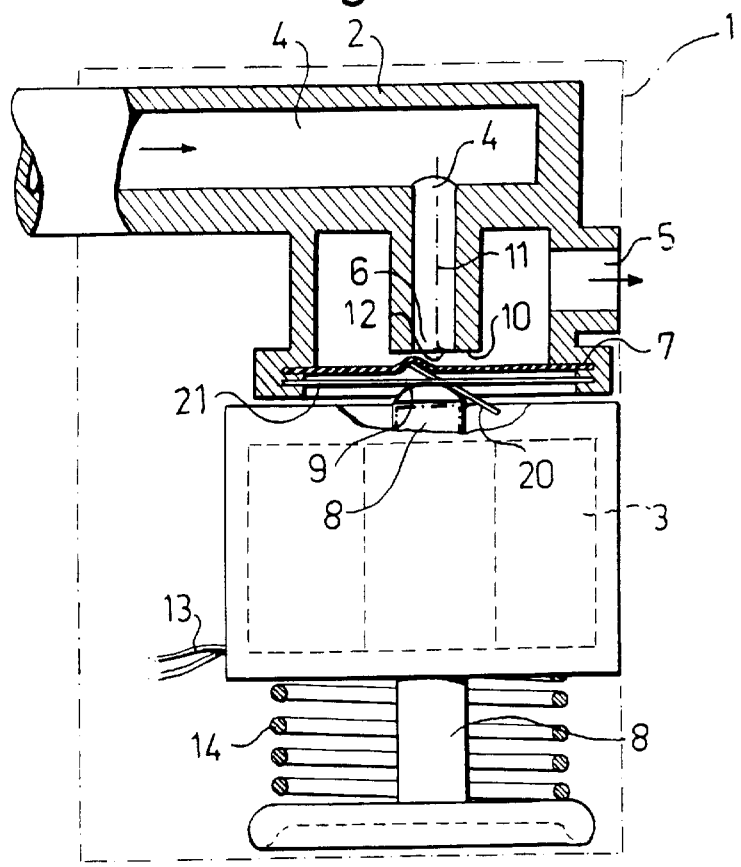
FIG. 6 is a section through an inventive valve, with another embodiment of the sealing actuator in a position in which the valve opening is open.

FIG. 6 depicts a valve corresponding to the valve which is depicted in FIG. 1 with the difference that the plane 10 of the valve seat 12 in this valve extends perpendicularly relative to its center axis 11. In this valve, a part 20 is arranged between the terminal side 9 of the solenoid shaft 8 and the valve seat 12, this part being situated obliquely with respect to the valve seat 12. The part 20 can be a part of a spiral disk 21 (detailed below) secured in the valve housing. As shown in FIG. 6, the membrane can be attached between the disk 21 and the valve seat 12. The plane of the shaft end 9 can be arranged parallel to the plane 10 of the valve seat 12, as illustrated with the dashed lines, but is preferably rounded. The procedure in the opening and closing of the valve seat is approximately the same as has been described in connection with FIG. 4 and has the advantages obtained in connection therewith.

Figure 7:
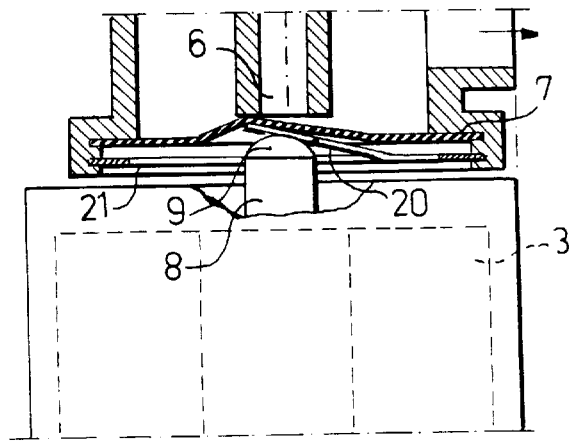
FIG. 7 is a partial section through a valve according to FIG. 6, with the sealing actuator in a partially open position.

FIG. 6 depicts the valve opening 6 in an open position. FIG. 7 depicts the valve opening 6 in a half-open position in which the shaft end 9 is pressing the membrane 7 against a portion of the valve seat 12 by means of the part 20 in order to subsequently gradually close the valve opening 6. As previously described, a gap arises between the membrane 7 and the valve seat 12 at the moments of opening and closing, respectively.

FIG. 8 shows a plan view of a disk 21 with the obliquely formed part 20. The disk 21 consists of a material so that in all positions, it tends to assume the oblique position depicted.

FIG. 9 depicts a lateral view of the disk 21. The obliquely situated part 20 is disposed at an angle of between 5° and 40° preferably of 30° relative to the plane of the disk 21.

FIGS. 10 and 11 depict an alternative disk 22 with a leaf spring 23 and an obliquely arranged part 24.

The seal thus far has been described in the form of a membrane which is secured in the valve housing. In the context of the invention, in cases where it is possible, a seal which is preferably applied at the valve seat, at the terminal side of the solenoid shaft, or at the obliquely arranged part, can be used instead of a membrane. The membrane can also be combined with such seal. In such cases the membrane is merely a movable separating wall between the solenoid and the valve housing which prevents gas from leaking into the solenoid.

Figure 12:
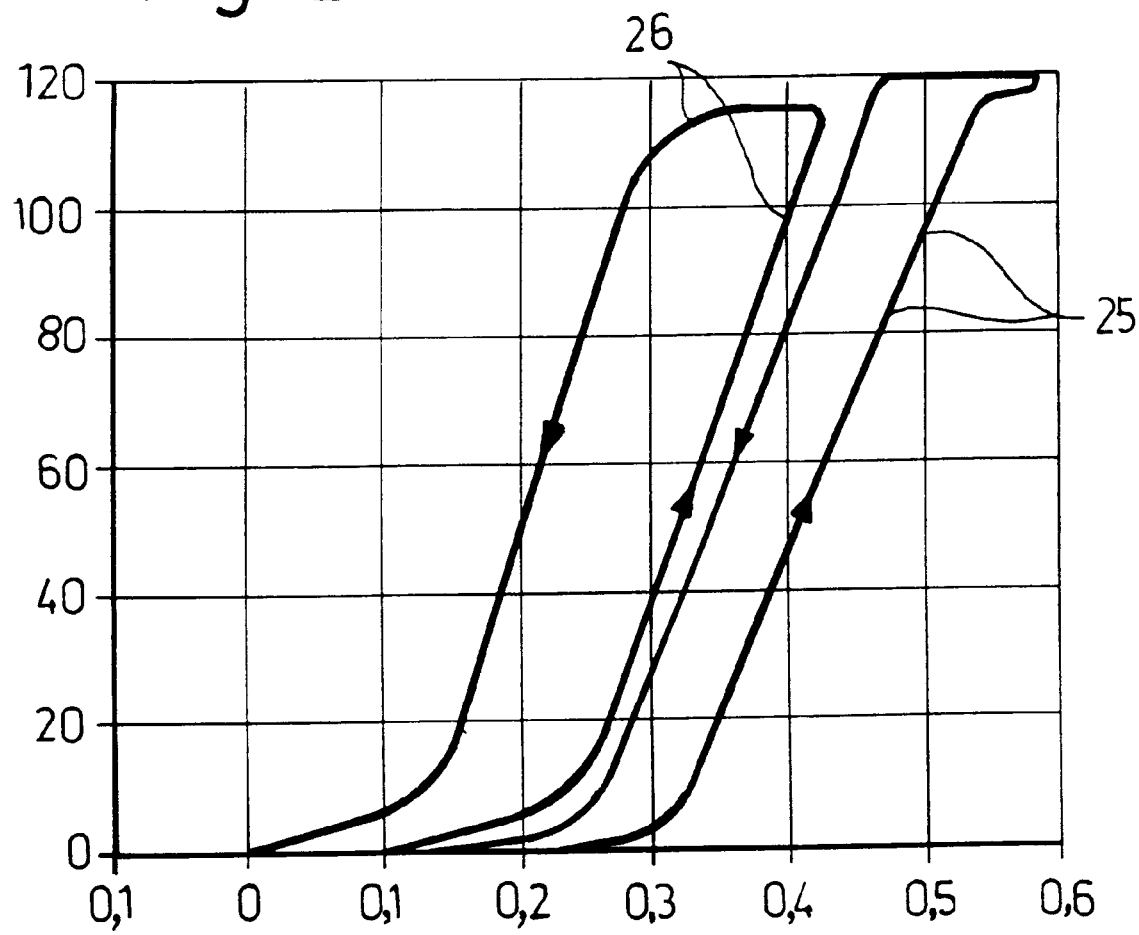
FIG. 12 is a gas flow diagram illustrating gas flow through the inventive valve.

FIG. 12 graphically shows gas flows, with gas flow/min. being depicted along the vertical axis, and the voltage fed to the solenoid shaft 8 being depicted along the horizontal axis. The right flow curve 25 describes a flow characteristic of a valve according to the prior art, and the left flow curve 26 describes a flow characteristic of an inventive valve. A sharp bend at the rising curve of the right flow curve 25 shows that a relatively abrupt opening of the valve opening occurs. The falling curve also shows, by means of a sharp bend, that an abrupt closing of the valve opening occurs. The flow curve 25 also shows the problems in connection with a known valve, particularly the regulating of small flows with a high precision and reproducibility. The left curve 26 shows how a gradual opening and closing of the valve opening in an inventive valve can change the contour of the curve. The curve 26 proceeds continuously, a relatively soft transition from a closed position into an open position, and vice versa, being achieved.

By means of the described gradual opening and closing of the valve opening, which begins or ends with the previously described gap between the valve seat and the seal, particularly small amounts of gas can be regulated with a high precision and reproducibility and with a large dynamic.

Although modifications and changes may be suggested by those skilled in the art, it is the intention of the inventors to embody within the patent warranted hereon all changes and modifications as reasonably and properly come within the scope of their contribution to the art.

What is claimed is:

1. A valve for regulating a gas flow comprising:

a valve housing having an inlet for a gas to be regulated and an outlet for a regulated gas flow;

a valve seat with a valve opening disposed in said valve housing between said inlet and said outlet;

a movable sealing element disposed in front of and spaced from said valve seat and said valve opening, said sealing element having a first side facing said valve seat and said valve opening, and a second side opposite said first side;

a movable sealing actuator disposed at said second side of said sealing element and operable to move said sealing element in a first direction through a distance for decreasing a flow of said gas through said valve opening and in a second direction, opposite said first direction, for increasing a flow of said gas through said valve opening; and a preformed part mounted in said housing between said sealing actuator and said sealing element, said preformed part having at least a portion thereof disposed at a non-zero angle relative to said valve seat and said portion having a surface area which is substantially equal to a surface area of said valve seat, said sealing actuator having a terminal side interacting with said preformed part to press said preformed part against said second side of said sealing element during movement of said sealing element through said distance in said first direction to gradually cause said first side of said sealing element to make contact with said valve seat and, when said sealing element is moved through said distance in said second direction, causing said first side of said sealing element to gradually detach from said valve seat.

2. A valve as claimed in claim 1 wherein said terminal side of said sealing actuator has a surface area which is smaller than the surface area of said valve seat.

3. A valve as claimed in claim 2 wherein said terminal side of said sealing actuator is rounded.

4. A valve as claimed in claim 1 wherein said terminal side of said sealing actuator and said valve seat are disposed in respective planes which are parallel.

5. A valve as claimed in claim 1 wherein said preformed part comprises a spiral disk.

6. A valve as claimed in claim 2 wherein said preformed part comprises a leaf spring.

7. A valve as claimed in claim 1 wherein said non-zero angle comprises an angle in a range between 5° and 40°.

8. A valve as claimed in claim 1 wherein said non-zero angle comprises 30°.

\* \* \* \* \*